United States Patent
Guenkel et al.

[11] Patent Number: 5,313,009
[45] Date of Patent: May 17, 1994

[54] NITRATION PROCESS

[75] Inventors: Alfred A. Guenkel; John M. Rae, both of Vancouver; Edward G. Hauptmann, West Vancouver, all of Canada

[73] Assignee: NRM International Technologies C.V., Utrecht, Netherlands

[21] Appl. No.: 135,569

[22] Filed: Oct. 14, 1993

Related U.S. Application Data

[63] Continuation-in-part of Ser. No. 863,315, Apr. 1, 1992, abandoned, which is a continuation of Ser. No. 619,151, Nov. 28, 1990, abandoned, and a continuation-in-part of Ser. No. 461,142, Jan. 4, 1990, abandoned.

[51] Int. Cl.$^5$ .................. C07C 201/00; B01D 3/00
[52] U.S. Cl. .................. 568/927; 568/928; 568/929; 568/932; 568/937; 568/939; 203/12
[58] Field of Search ............ 568/927, 929, 928, 932, 568/937, 939, 940; 203/12

[56] References Cited

U.S. PATENT DOCUMENTS

| | | | |
|---|---|---|---|
| 2,256,999 | 9/1941 | Castner | 568/933 |
| 3,928,475 | 12/1975 | Dassel | 568/939 |
| 3,981,935 | 9/1976 | McCall | 568/939 |
| 4,021,498 | 5/1977 | Alexanderson et al. | 568/939 |
| 4,091,042 | 5/1978 | Alexanderson et al. | 568/939 |
| 4,331,819 | 5/1982 | McCall | 568/939 |
| 4,496,782 | 1/1985 | Carr | 568/934 |
| 4,772,757 | 9/1988 | Lailach et al. | 568/939 |
| 4,973,770 | 11/1990 | Evans | 568/929 |
| 4,994,242 | 2/1991 | Rae et al. | 422/224 |

OTHER PUBLICATIONS

Kirk-Othmer, "Nitration," Encyclopedia of Chemical Technology, 3rd Edition, 1978, vol. 15.
Kirk-Othmer, "Nitrobenzene and Nitrotoluenes," Encyclopedia of Chemical Technology, 3rd Edition, 1978, vol. 15.

Primary Examiner—Shean Wu
Attorney, Agent, or Firm—Breiner & Breiner

[57] ABSTRACT

A continuous process to nitrate a nitratable aromatic compound in a nitronium ion solution in a nitrator. The process comprises feeding into the nitrator nitronium ion solution of a composition within an area defined by connecting three points in a ternary phase diagram of nitric acid, sulfuric acid and water. The three points correspond to first about 82% of sulfuric acid and 18% nitric acid, secondly about 55% sulfuric acid and about 45% water and, thirdly, 100% sulfuric acid, with the nitric acid preferably being below about 3%. The nitratable aromatic compound is introduced in a manner such that a fine emulsion of hydrocarbon in the nitronium ion solution is formed with the hydrocarbon evenly distributed in the acid phase. The acid and the nitratable aromatic compound are brought into intimate contact in a plug-flow nitrator that contains mixing elements.

15 Claims, 3 Drawing Sheets

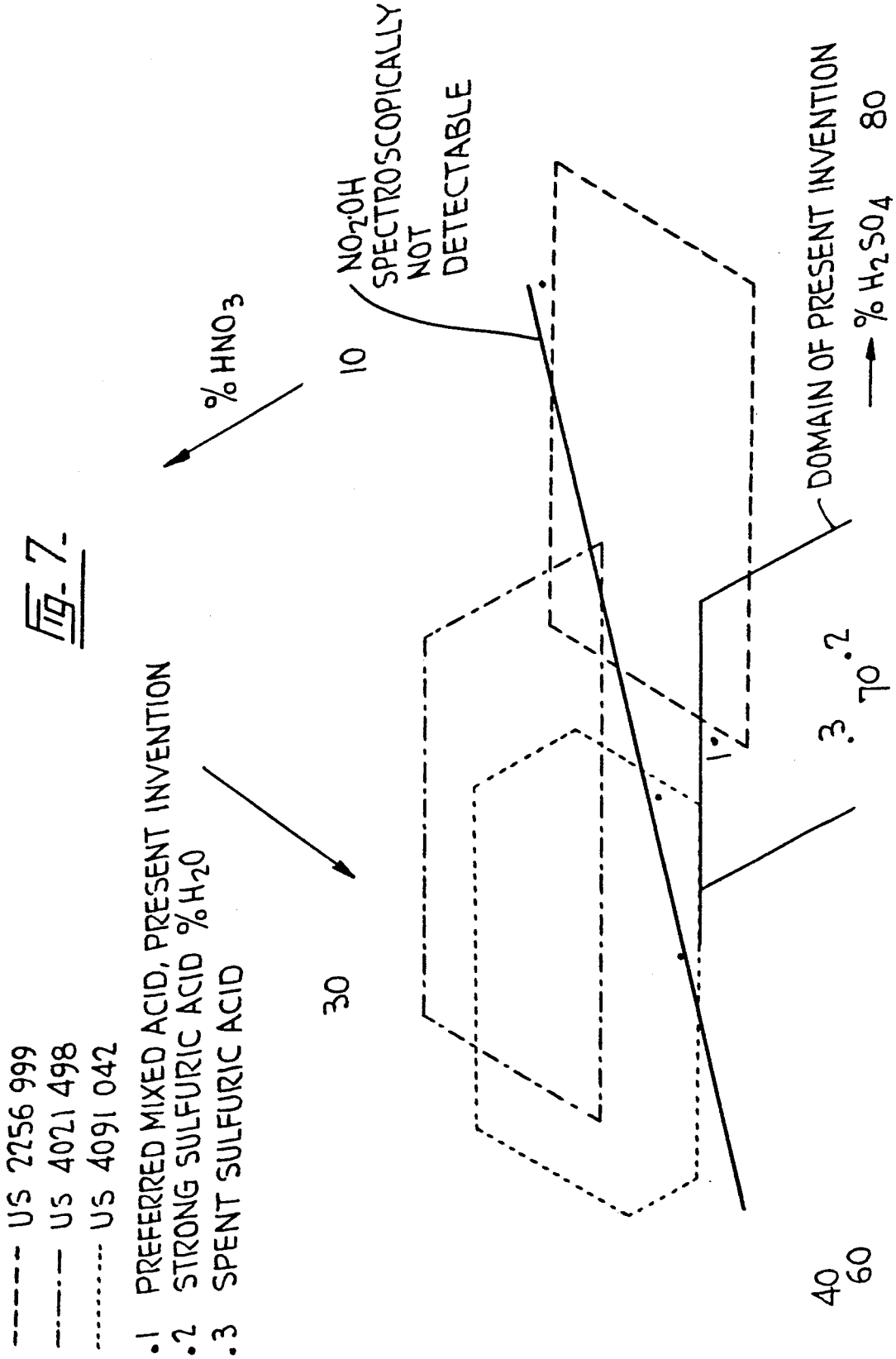

NITRATION PROCESS

RELATED APPLICATIONS

This application is a continuation-in-part of Alfred A. Guenkel et al, U.S. Ser. No. 07/863,315 filed Apr. 1, 1992 now abandoned, which, in turn, is a continuation of U.S. Ser. No. 07/619,151 filed Nov. 28, 1990, now abandoned; and a continuation-in-part of U.S. Ser. No. 07/461,142 filed Jan. 4, 1990, now abandoned.

FIELD OF THE INVENTION

This invention relates to a continuous process to nitrate nitratable organic compounds, particularly for the preparation of mononitrobenzene. According to the nitration process utilizing nitric acid and sulfuric acid, the concentration of nitric acid ($HNO_3$), sulfuric acid ($H_2SO_4$) and water is controlled so that the nitric acid is substantially fully dissociated into nitronium ions.

DESCRIPTION OF THE PRIOR ART

Nitrated aromatic hydrocarbons and nitrated halogenated aromatic hydrocarbons, and particularly mononitrobenzene, are important chemical intermediates. The technology of manufacturing these compounds is well established and is discussed in a number of books, for example in Kirk-Othmer, "Encyclopedia of Chemical Technology," 3rd Edition, 1978, Vol. 15 in the articles entitled "Nitration" and "Nitrobenzene and Nitrotoluenes." Moreover, many industrial manufacturing processes for these compounds have been developed, yet nitration is still an active field of research in an effort to improve the commercial production of aromatic nitro compounds, particularly mononitrobenzene, without associated by-products such as dinitrobenzene which adversely affects the manufacture of aniline, and dinitrophenol isomers and picric acid, which are disadvantageous because of the need to remove and treat.

One approach to an improved process is an adiabatic nitrobenzene process, first described by Castner in U.S. Pat. No. 2,256,999 as a batch process and later described in U.S. Pat. Nos. 4,021,498 and 4,091,042, both to Alexanderson et al, as a continuous process. The first Alexanderson patent, i.e., the '498 patent, discloses an atmospheric, adiabatic process with the invention being based on the selection of a specific mixed acid containing from 5 to 8.5 percent nitric acid, about 60 to 70 percent sulfuric acid and not less than about 25 percent water. By using this mixture of acid, the adiabatic process is carried out at a temperature in the range of about 40° to 80° C. for a period of about 0.5 to 7.5 minutes. The second Alexanderson et al reference, i.e., the '042 patent, is an improvement on the disclosure of the '498 patent and requires a mixed acid containing from 3 to 7.5 percent of nitric acid, from about 58.5 to 66.5 percent of sulfuric acid and from about 28 to 37 percent water. The reaction temperature can be from about 80° to 120° C. However, the process is carried out at superatmospheric pressure.

Although the continuous adiabatic process described in the aforesaid Alexanderson patents have received substantial commercial interest, the processes described are still not fully satisfactory from the commercial standpoint. With respect to the process described in the '498 patent, unacceptably large concentrations of dinitrobenzene are formed and further substantial amounts of the dinitrophenols and trinitrophenols (picric acid) are formed. It is believed that the problems associated with the process result from either too little water in the mixed acid or to the use of too great a concentration of sulfuric acid, leading to the formation of the excessive by-products. As to the '042 patent, it has been found that the processing conditions lead to reduced conversion efficiencies, slow reaction rates and substantial losses of nitric acid.

Accordingly, there is a need for a continuous nitration process which does not suffer from the aforesaid disadvantages.

SUMMARY OF THE INVENTION

The present invention provides a continuous process to nitrate a nitratable aromatic compound typically an aromatic hydrocarbon or a halogenated hydrocarbon, and particularly benzene, in which the formation of oxidation by-products is substantially reduced compared with the prior art, and wherein the reaction rate is substantially increased.

Accordingly, the present invention provides a continuous process to nitrate a nitratable aromatic compound by mixed nitric and sulfuric acids in the presence of water in a nitrator. The process comprises:

(a) introducing into the nitrator a nitronium ion solution of a composition that contains nitric acid, water and sulfuric acid, and lies within an area defined by three points A, B and C of a ternary phase diagram of nitric acid, sulfuric acid and water where:

A corresponds to about 82% of sulfuric acid and 18% nitric acid;

B corresponds to about 55% sulfuric acid and 45% water; and

C corresponds to 100% sulfuric acid; such composition being selected so that nitric acid is substantially fully dissociated to nitronium ion and the sulfuric acid strength is sufficiently high to permit a temperature at the inlet of the nitrator of from about 97° to 120° C.;

(b) allowing the nitratable aromatic compound to commingle with the nitronium ion solution so as to provide a fine emulsion of the aromatic compound within the nitronium ion solution with the aromatic compound being evenly distributed in the nitronium ion solution;

(c) causing the nitronium ion solution containing the nitratable aromatic compound to react at a temperature at the inlet of the nitrator or a series of nitrators of from about 97° to 120° C. in a nitrator containing mixing elements able to achieve and to maintain mixing of the contents of the nitrator to nitrate the nitratable compound, the residence time in the nitrator to achieve approximately 90% conversion being about 25 seconds and about 70 seconds to achieve essentially 100% conversion, to provide an aromatic nitro compound containing only low levels of impurities.

The preferred concentrations for operation are in the range 0.5% and up to 3.0% nitric acid; 27.0 to 33.0% water, with sulfuric acid making up to 100%. The present invention is based on the discovery that the nitric acid must be substantially fully dissociated to the nitronium ion and the sulfuric acid strength be maintained sufficiently high to control the temperature at the inlet of the nitrator and thereafter allowing the nitratable aromatic compound to commingle with the nitronium ion solution so as to provide a fine emulsion of the aromatic compound so that the aromatic compound is evenly distributed, causing the nitronium ion solution containing the nitratable aromatic compound to react and controlling the residence time in the nitrator to provide for only low levels of impurities. The critical feature according to the present invention is the discovery that the nitric acid is present in lower levels than previously thought possible, i.e., at concentrations of less than about three percent.

According to the present invention, it has also been found that the use of a plug-flow or pipe nitrator and the dispersion of the hydrocarbon throughout are advantageous in carrying out the process of this invention. A particularly desirable reactor is described in Rae et al, U.S. Pat. No. 4,994,242 issued Feb. 19, 1991.

Features of the present invention, therefore, include selecting the sulfuric acid concentration so that the reaction could be carried out at a temperature at the inlet of the nitrator of 97° to 120° C. without having a super-atmospheric pressure; selecting the ratio of nitric acid, water and sulfuric acid so that the nitric acid is preferably below about 3% and is substantially fully dissociated to nitronium ion, and commingling the nitratable aromatic compound with the nitronium ion solution so as to provide a fine emulsion with the aromatic compound being substantially evenly distributed within the nitronium ion solution, whereby the reaction can be carried out at a high temperature and at atmospheric pressure to lower the residence time within the nitrator to provide product having only low levels of impurities.

Having described the invention in general terms, the presently preferred embodiments will be described in reference to the drawing.

BRIEF DESCRIPTION OF THE DRAWINGS

In the drawing,

FIG. 7 is an amplification of the lower portion of the ternary system illustrated in FIG. 6 as it relates to the present invention and the prior art.

Referring now to FIG. 1, which shows schematically a single hydrocarbon droplet 10 of diameter Di surrounded by a shell 12 of diameter Do of mixed acid, the nitration process on a microscale is visualized as follows:

Figure 1:
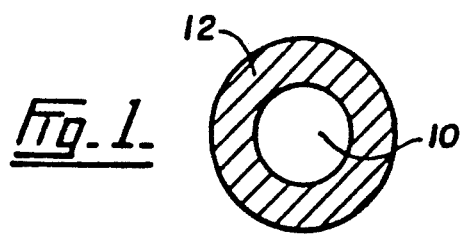
FIG. 1 shows a droplet of dispersed hydrocarbon surrounded by a concentric shell of nitronium ion solution.

(i) Under operating conditions typical in an adiabatic nitration process, the volumetric phase ratio of the hydrocarbon to nitric mixed acid phases is about one to four. Thus, if each hydrocarbon droplet is visualized to be surrounded by an "acid shell," the ratio of the diameters Di/Do of the hydrocarbon to the diameter Do of the acid shell is 1/1.71. At a given volumetric fraction of the hydrocarbon this ratio does not depend on the size of the hydrocarbon droplet, but it will vary if the volumetric fraction is changed. The lengths of the diffusion paths to the interface from the hydrocarbon phase and from the acid phase are of the same order of magnitude.

(ii) Once a hydrocarbon droplet has been created, the nitration reaction will take place at the interface. This requires that the nitronium ion, $No_2^+$ diffuses to the interface.

(iii) When the nitration process is run with excess hydrocarbon on a molar basis, there will always be a large excess of unreacted hydrocarbon at the interface. At the start of the nitration the molar concentration of the unreacted hydrocarbon in the hydrocarbon phase is 100 percent, while that of the nitronium ion in the acid phase could be about 3 percent or less. When the nitration reaction approaches completion, the molar concentration of the nitronium ion approaches zero while there remains still an appreciable amount of unreacted hydrocarbon. Therefore, diffusion of hydrocarbon inside the hydrocarbon phase is not a significant factor in the overall reaction rate.

(iv) If the hydrocarbon droplet is created in a mixed acid where nitric acid is present only as the reactive species, i.e., the nitronium ion, then diffusion of undissociated nitric acid into the organic phase cannot take place. Therefore, oxidation side reactions, other than those going through a mechanism involving the nitronium ion, are largely eliminated.

(v) The nitration reaction at the interface is very fast so that neither the nitronium ion can penetrate into the hydrocarbon phase, nor can unreacted hydrocarbon penetrate more than a few molecular diameters into the acid phase except when the nitration reaction approaches completion or when the intrinsic homogeneous nitration rate is very slow. Any hydrocarbon initially present in the acid phase will be quickly nitrated, the acid phase will essentially be saturated with the nitrocompound during all stages of the nitration process.

(vi) Dinitration, which is a much slower reaction than the mononitration, will take place mostly in the acid phase as dissolved mononitro compounds react with the nitronium ion. Dinitration, a homogeneous, kinetically controlled process, competes for nitronium ions with mononitration, a process controlled by diffusion of the nitronium ion to the interface and by the solubility of the hydrocarbon in the acid phase. Dinitration can be controlled by altering the rate of mononitration which consumes the nitronium ion. This rate of mononitration can be altered by, for example, increasing the area of the interface by creating a finer emulsion using an appropriate nitrator design.

(vii) Bulk mixing is an important aspect of nitration in that it is responsible for the creation of small hydrocarbon droplets and in that it disperses the reactants fed into the nitrator. However, once a droplet has been created, the rate of nitration in its environment is dictated by diffusion in the acid shell surrounding each droplet, with occasional bulk mixing and coalescence of drops. Bulk mixing in a typical commercial scale nitrator of the back-mix type is a relatively slow process and, for this reason, there is ample opportunity for partially nitrated hydrocarbon to establish contact with the concentrated feed mixed acid. Such intimate contact may lead to diffusion of undissociated nitric acid into the hydrocarbon phase, if those species are present, and subsequent oxidation.

(viii) Once the hydrocarbon has been dispersed uniformly in the acid phase, then the nitration reaction can be viewed as an unsteady process of mass transfer of the nitronium ion to the interface in the acid shell surrounding each hydrocarbon droplet.

Thus, the nitronium ion is yielded from protonation and subsequent dissociation of nitric under strongly acidic conditions. The mechanism of nitronium ion formation and its electrophilic substitution onto the benzene molecule can be represented by the following schemes:

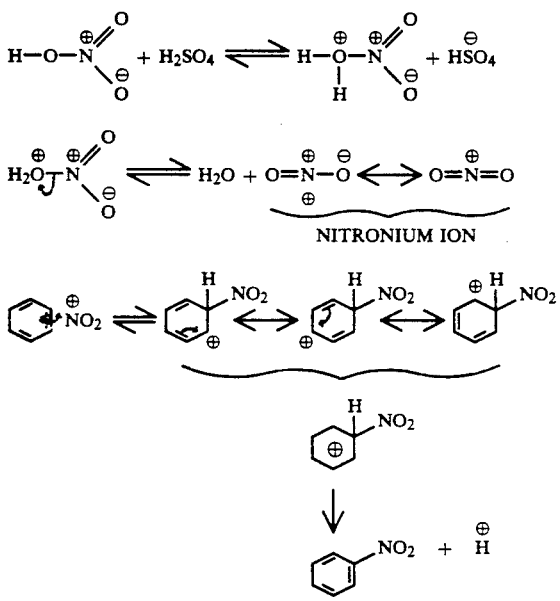

Without intending to be bound by theory, it is believed the unexpectedly beneficial outcome of the improved process of the present invention is based on the relatively greater availability of reactive species, namely nitronium ion, as follows:

(a) Kinetics

The mechanism of nitronium ion formation is controlled by two equilibria, which can be described by the constants $K_1$ and $K_2$, where -

$$K_1 = \frac{[H_2NO_3^\oplus][HSO_4^\ominus]}{[HNO_3][H_2SO_4]} \text{ and, } K_2 = \frac{[NO_2^\oplus][H_2O]}{[H_2NO_3]^\oplus}$$

Relatively, the reaction expressed by $K_1$ is slow compared with that covered by $K_2$. It can be seen, therefore, that if $H_2SO_4$ concentration is increased, then the concentration of protonated nitric acid must also increase, which in turn leads to a greater availability of nitronium ion. This is borne out experimentally in that it was discovered that a very small increase in the concentration of sulfuric acid, a catalyst, could more than compensate for a significant decrease in concentration of actual reagent, that is, nitric acid. In specific terms, these findings are contrary to claims made in prior art processes, in which it is stated that it is uneconomical to operate with a concentration of $HNO_3$ below 3% in the mixed acid due to reduced reaction rates, and that it is inadvisable to run with levels of water less than 28%, due to excessive formation of by-products.

(b) By-Products

It is well established that nitrophenols are formed from phenol, which results from oxidation of benzene by $HNO_3$. Once formed, it is also well known that phenol will rapidly nitrate. The present process results in a dramatic reduction in the level of nitrophenols produced, and essentially eliminates the formation of picric acid (PA). Again, theory and practice are entirely compatible in that by operating in the range described, the present process sharply reduces the level of undissociated $HNO_3$ in the mixed acid. This finding also disproves conventional wisdom as described in prior art processes.

Figure 6:
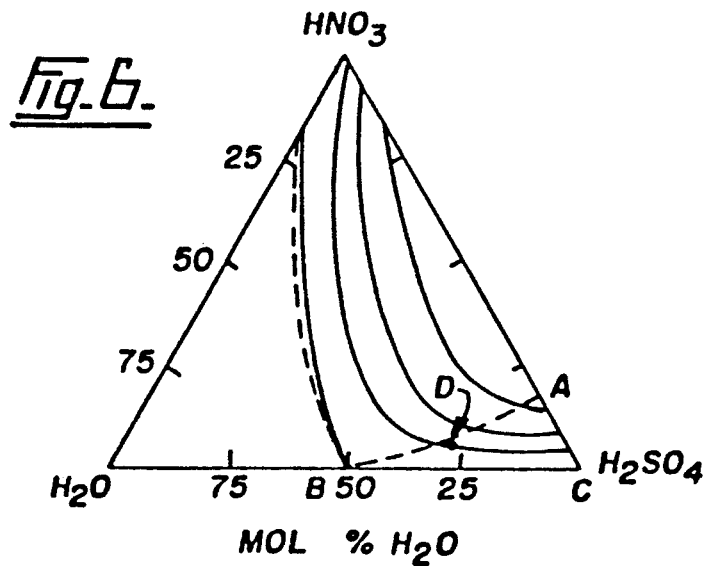
FIG. 6 is a ternary phase diagram for the system water-nitric acid-sulfuric acid.
Figure 2:
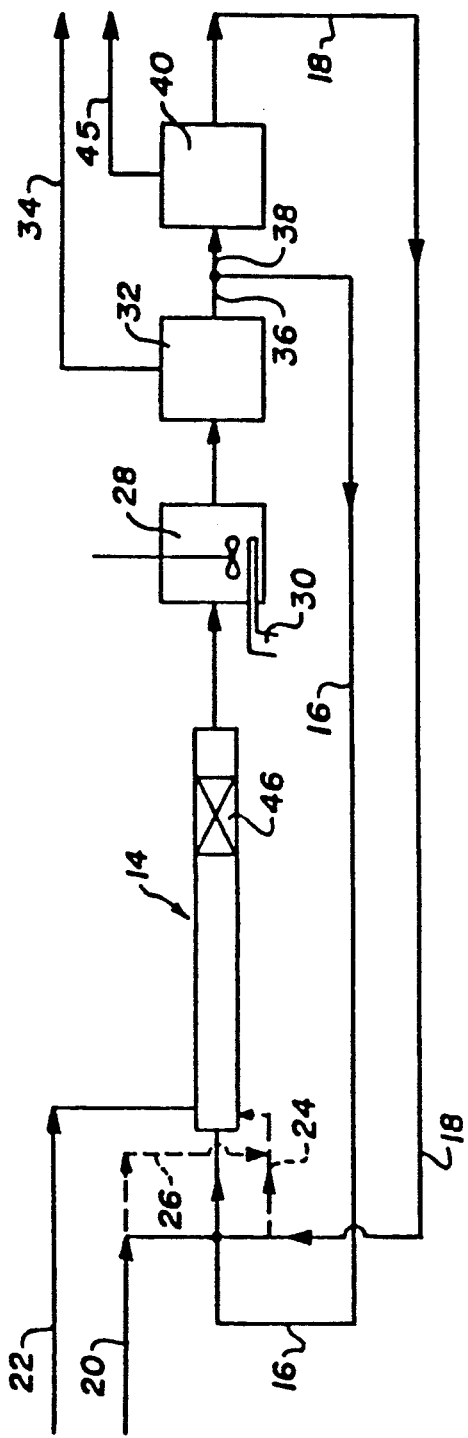
FIG. 2 illustrates a first embodiment of the invention in which a nitration process is carried out in the isothermal mode.

FIG. 2 shows a flow diagram for an isothermal nitration process. A pipe nitrator 14 receives recycle spent sulfuric from conduit 16, reconcentrated sulfuric acid from conduit 18, nitric acid from conduit 20 and hydrocarbon to be nitrated from conduit 22. The acid steams are blended in a ratio such that the resulting mixed acid contains nitric acid mostly in the form of the reactive species, the nitronium ion. Mixed acids where undissociated acid cannot be detected spectroscopically can approximately be mapped on the ternary diagram shown in FIG. 6 by connecting the three points A, B and C. A corresponds to a composition of about 82% sulfuric acid and 18% nitric acid; B corresponds to a composition of about 55% sulfuric acid and 45% water, and C corresponds to 100% sulfuric acid. The solid lines in FIG. 6 are lines of constant nitronium ion concentration; the dashed line in the right-hand corner maps the region where nitric acid is fully dissociated. Finally, a second dashed line running in close proximity to a solid line, the line suggesting zero nitronium ion concentration, delineates the limits of nitration of mononitrobenzene. In FIG. 6 the area bounded by A,B,C indicates those mixed acid/water compositions in which $NO_2OH$, undissociated nitric acid, is not detectable. In other words, it is in these compositions where maximum dissociation of nitric acid to nitronium ion is observed. Thus, the mixed acid composition preferred according to the present invention is embraced by the shaded area.

A further appreciation of this can be gained by amplification of the lower portion of the ternary system, which is shown in FIG. 7. From this diagram, it is now concluded readily that mixed acid compositions defined by the Alexanderson patents are largely not in that region which provides maximum availability of nitronium ion.

The three acid streams from conduits 16, 18, and 20 may be mixed in line before entering the pipe nitrator 14. Alternatively, a slip stream of reconcentrated sulfuric acid can be introduced through conduit 24 and may be blended with a nitric acid supplied from conduit 26 and be introduced separately from the recycle sulfuric acid.

The pipe nitrator 14 discharges to a stirred tank type of nitrator 28 having provision for cooling via conduit 30. The process fluids, nitrated hydrocarbon and spent acid flow from nitrator 28 to a gravity separator 32. The product nitrocompound is discharged from the separator 32 via conduit 34 while the spent acid is delivered via conduit 36 and is subsequently split into a recycle stream for conduit 16 and a stream for conduit 38 leading to a sulfuric acid concentrator 40. In the sulfuric acid concentrator 40 water is removed via conduit 45 while reconcentrated sulfuric acid is recycled through conduit 18. The sulfuric acid concentrator 40 may be omitted and in this case spent acid is disposed and strong sulfuric acid is imported.

It may be an advantage to install mixing elements 46 inside the pipe nitrator 14.

Figure 3:
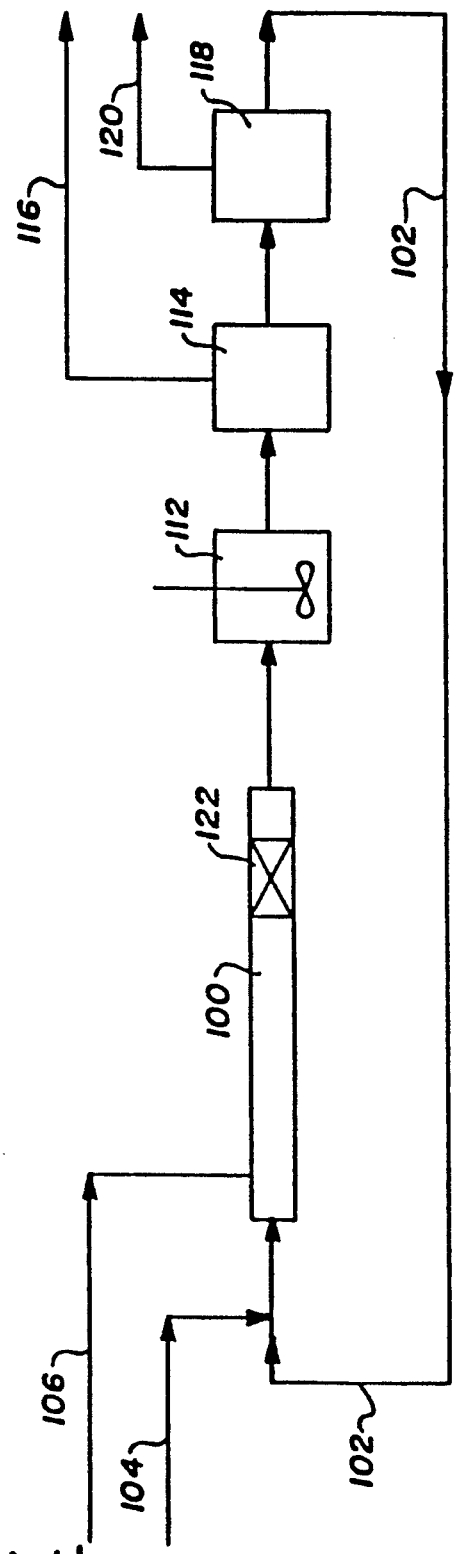
FIG. 3 illustrates a second embodiment of the invention in which a nitration process is carried out in the adiabatic mode.

FIG. 3 shows a nitration process operating under adiabatic conditions. A pipe nitrator 100 receives reconcentrated sulfuric acid from conduit 102, nitric acid from conduit 104 and hydrocarbon to be nitrated from conduit 106. The acid streams are again blended in a ratio such that the resulting mixed acid contains nitric acid mostly in the form of the reactive species, the nitronium ion. The two acid streams from conduits 102 and 104 may be mixed in line before entering the pipe nitrator 100 or may be introduced separately into the pipe nitrator 100. The pipe nitrator 100 discharges to a stirred tank type of nitrator 112. In cases where the reaction rate is very fast, which is specific to the hydrocarbon species to be nitrated and specific to the operating conditions, the reaction may go essentially to completion inside the pipe nitrator 100 so that the stirred tank type of nitrator 112 is not required. In cases where the nitration rate is slow the pipe nitrator 100 serves mainly as a hydrocarbon dispersion device. Fresh nitrating acid entering the stirred tank nitrator 112 is intimately mixed with fresh hydrocarbon. The process fluids pass to a separator 114 and product nitrocompound is discharged from separator 114 via conduit 116 while the spent acid is delivered to a sulfuric acid concentrator 118. In the sulfuric acid concentrator 118 water is removed via conduit 120 while reconcentrated sulfuric acid is recycled to the pipe nitrator 100 via conduit 102.

Again, it may be advantageous to install static mixing elements 122 inside the pipe nitrator 100.

A key difference between the isothermal process shown in FIG. 3 and the adiabatic process of FIG. 3 is that energy is rejected from the isothermal process through the cooling water of junction 30, while no energy is rejected from the adiabatic process. Therefore, the heat of nitration is available in the acid concentrator 118 of the adiabatic process.

Figure 4:
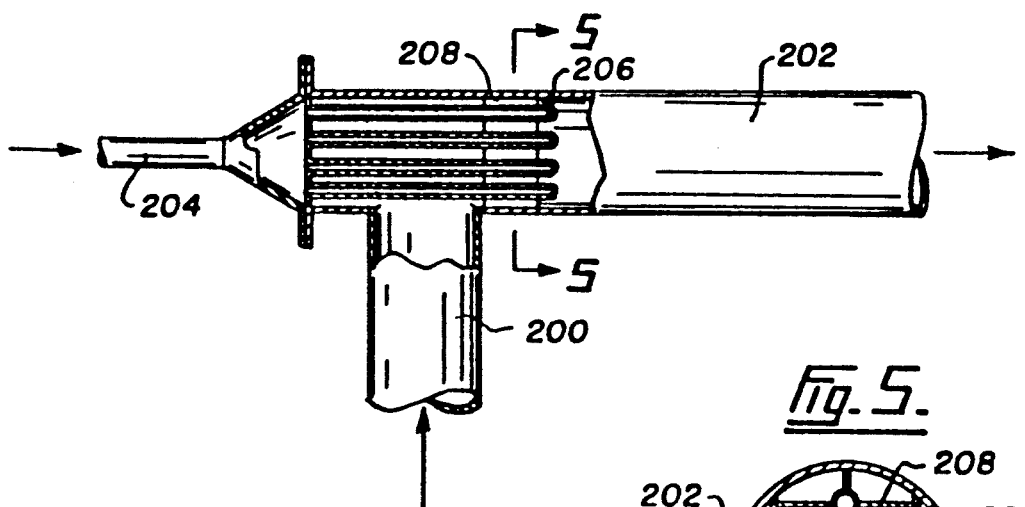
FIG. 4 illustrates an apparatus used to carry out the nitration process.
Figure 5:
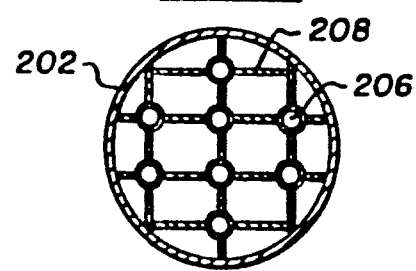
FIG. 5 is a section in the line 5—5 in FIG. 4.

FIGS. 4 and 5 show an apparatus used to disperse the hydrocarbon into the acid phase. Acid is introduced through a side-port 200 into a plug flow or pipe nitrator 202. The diameter of the pipe nitrator 202 is selected to establish flow in the turbulent regime which is usually assumed to prevail at Reynolds numbers larger than 4000. Into this turbulent acid stream inside the pipe nitrator 200 the hydrocarbon stream is introduced through port 204 and is distributed through a number of evenly spaced feed systems 206. The feed systems 206 are small diameter pipes closed at one end but each provided with a number of openings which may be small holes drilled into the end. Baffles 208 are provided to stiffen the feed systems 206 and to assure even distribution of the acid flow at the cross-section where the hydrocarbon enters the acid phase. Normally one feed system per square inch of cross-sectional area of the pipe nitrator 200 is sufficient. The number or distribution of the feed systems is dictated more by considerations relating to mechanical fabrication than by process requirements. The nitration process demands the creation of a hydrocarbon dispersion and an even distribution of the hydrocarbon within the constraints of practical fabrication techniques. The number and size of the openings provided are selected on the basis of common design practice, apparent to those skilled in the art.

Many embodiments of the hydrocarbon inlet system are feasible. Examples include a simple sparger ring or a sparger tube.

Operating temperatures and acid strengths used in the process of this invention are set by consideration of kinetics and safety, both being specific to the hydrocarbon being nitrated. In an adiabatic nitration process the acid temperatures are also set by the requirements to match safe nitrating conditions with the operating temperatures of a sulfuric acid concentrator, typically a vacuum flash concentrator. Such a match has been disclosed in prior art processes; however, through the invention disclosed in this process it has become possible to operate at mixed acid strengths previously not considered feasible without producing excessive amounts of by-products. The present invention makes it possible to reach the same conversion as that obtained in prior art processes requiring only a small fraction of the residence time required in the reactors of prior art processes. This result, which implies substantial capital savings, can be achieved while simultaneously reducing the rate of formation of by-products, in particular of picric acid. In terms of by-product formation analytical results from two sets of representative process conditions are compared in Table 1. Table 1 is as follows:

TABLE 1

INDUSTRIAL SCALE COMPARISON OF CONVENTIONAL ADIABATIC PROCESS AND PROCESS OF PRESENT INVENTION

| | CONVENTIONAL ADIABATIC PROCESS Mixed Acid | | | PROCESS OF PRESENT INVENTION Mixed Acid | | |
|---|---|---|---|---|---|---|
| | % HNO3 4.5 | % H2SO4 63.5 | % H2O 32.0 | % HNO3 2.8 | % H2SO4 69.5 | % H2O 27.7 |
| Impurities in Crude Product [PPM] | | | | | | |
| DNB | | 50 | | | 50 | |
| DNPH | | 1500 | | | 1700 | |
| PA | | 3000 | | | Trace or non-detectable levels | |
| Total NITROPHENOLS | | 4500 | | | 1700 | |

DNB - Dinitrobenzene
DNPH - Dinitrophenol
PA - Picric Acid (Trinitrophenol)

Comparison of the two sets of results clearly denotes a radical adjustment to the basic chemistry. This is reflected by almost a three-fold decrease in formation of nitrophenols from that of the prior art process. Further-more, the present system results in the virtual elimination of PA in the reaction products.

Thus, the process of the present invention is characterized by a number of features not found in the prior art. The mixed acid composition in the present process is selected so that nitric acid is more fully dissociated to nitronium ion and the sulfuric acid strength is pushed as high as possible to take advantage of the higher nitration rates. Mixed acids useful in the process of the present invention can have compositions where the nitric acid is below 3%, such as the compositions:

|                 | 1      | 2     | 3     |
|-----------------|--------|-------|-------|
| $H_2SO_4$       | 72.02% | 68.0% | 69.5% |
| $HNO_3$         | 2.99%  | 2.8%  | 2.8%  |
| $H_2O$          | 24.99% | 29.2% | 27.7% |

These mixed acids, basically nitronium ion solutions, serve only as examples to demonstrate that the process of this invention can be operated with acids not previously known in the art. However, many other acid compositions may be used including acids proposed in prior art processes but where the nitric acid is substantially fully dissociated.

The strength of the reconcentrated sulfuric acid required to produce mixed acid under column 2 above is about 70.6%. FIG. 6 shows the region for complete nitric acid dissociation which is obtained for compositions falling at the lower right hand corner in the area of the diagram defined by points A, B and C falling below the dashed line. Point D is the composition of an example of a nitronium ion solution suitable to be used in the process of the present invention.

The residence time in the process of the present invention is short, made possible because -
(i) the nitrator inlet temperature can be higher than in the earlier processes, about 100° to 120° C. compared with about 95° C. in the prior art.
(ii) the strength of the reconcentrated sulfuric acid can be much higher than that used in earlier processes, about 71% sulfuric acid compared with about 68% in the prior art.
(iii) the benzene is introduced through feed systems which are uniformly distributed over the cross-section of the plug-flow nitrator.
(iv) dispersion of the hydrocarbon can be achieved through the use of mixing elements in a plug-flow reactor. In a particularly preferred embodiment that plug-flow reactor is as described and claimed in U.S. Pat. No. 4,994,242, the subject matter of which is incorporated herein by reference.

In the process of the present invention the nitrator operates under the static and dynamic head of the nitrobenzene-acid separator which operates at atmospheric pressure, but in the prior art the nitrator is pressurized to avoid flashing of benzene. The dynamic head loss through this plug-flow reactor can be established to avoid flashing of benzene. When the organic phase, mostly nitrobenzene, reaches the separator, its vapor pressure will be well below atmospheric. This is achieved by control of the final nitrator temperature through the amount of sulfuric acid circulating through the system.

Nitrogen oxides formed in the nitrators through oxidation side reactions are vented from the nitrobenzene acid separator of this invention which may operate at atmospheric pressure, thus reducing the inert load of the vacuum sulfuric acid concentrator. In the prior art these nitrogen oxides stay dissolved in the spent sulfuric acid going to the sulfuric acid concentrator where they contribute to the load on the vacuum system.

In the process of the present invention the energy required to maintain sulfuric acid strength in the nitration loop is supplied by preheating the nitric acid and benzene feeds to the nitrator using waste heat available in the washing and stripping areas of the plant. A start-up heater required in the nitration loop to bring the temperature of the circulating sulfuric acid up to it normal operating temperature can be very small. Its design basis is not set by the energy requirements of the nitration and acid concentration loop, but is rather dictated by the time necessary to bring the plant up to operating temperature.

The formation of dinitrobenzene in the process of the present invention can be controlled by adjusting the amount of excess benzene fed to the process. In the competing reaction of benzene and nitrobenzene, all nitric acid is consumed by the benzene before appreciable amounts of dinitrobenzene can form.

The rate of formation of dinitrophenol and picric acid can be controlled by acid composition and temperature in the nitration loop. The maximum temperature will be in the range of 120° to 135° C. The maximum temperature is selected to keep the vapor pressure of the process fluids in the nitrobenzene acid separator below 760 mm of mercury so that this separator can be operated at atmospheric pressure. Thus, the maximum operating temperature will depend on the spent acid composition and its vapor pressure and on the amount of excess benzene used and the partial pressure exerted by the benzene and nitrobenzene.

The rate of formation of dinitrophenol and picric acid can also be reduced by elimination of contact between nitric acid and nitrated aromatic. As mentioned, the mixed acid composition is selected to ensure complete dissociation of the nitric acid, the mixed acid is in fact a nitronium ion solution. Thus, no undissociated acid will be able to diffuse into the aromatic phase, where the oxidation reactions are known to occur. In the prior art processes nitric acid is only partially dissociated.

As will be apparent to one skilled in the art, various modifications can be made within the scope of the aforesaid description. Such modifications being within the ability of one skilled in the art form a part of the present invention and are embraced by the appended claims.

It is claimed:
1. A continuous atmospheric process to nitrate a nitratable aromatic compound in a nitronium ion solution in a nitrator, the process comprising:
(a) introducing into the nitrator a nitronium ion solution of a composition that contains nitric acid, water and sulfuric acid, and lies within an area defined by three points A, B and C of a ternary phase diagram of nitric acid, sulfuric acid and water where -
A. corresponds to about 82% of sulfuric acid and 18% nitric acid;
B. corresponds to about 55% sulfuric acid and 45% water; and
C. corresponds to 100% sulfuric acid; said composition being selected so that nitric acid is present below about 3% and is substantially fully dissociated to nitronium ion and the sulfuric acid strength is sufficiently high to permit a temperature at the inlet of the nitrator of from about 97° to 120° C.;

(b) allowing the nitratable aromatic compound to commingle with the nitronium ion solution so as to provide a fine emulsion of said aromatic compound within the nitronium ion solution with the aromatic compound being evenly distributed in the nitronium ion solution;

(c) causing the nitronium ion solution containing said nitratable aromatic compound to react at a temperature at the inlet of the nitrator of from about 97° to 120° C. in a nitrator containing mixing elements able to achieve and to maintain mixing of the contents of the nitrator to nitrate the nitratable compound to provide an aromatic nitro compound containing only low levels of impurities.

2. The process of claim 1 wherein said nitratable aromatic compound is mononitrobenzene.

3. The process of claim 2 wherein said composition is about 72.02% sulfuric acid, 2.99% nitric acid, and 24.99% water.

4. A process as claimed in claim 2 in which the nitronium ion solution is formed by mixing sulfuric and nitric acids prior to introduction into the nitrator.

5. A process as claimed in claim 2 wherein the nitric acid and the sulfuric acid are introduced into the nitrator separately.

6. A process as claimed in claim 2 wherein part of the spent sulfuric acid discharged from the nitrator is separated from the hydrocarbon phase, recycled to the nitrator and the remainder is reconcentrated or disposed of and replaced by strong make-up sulfuric acid.

7. A process as claimed in claim 2 in which fluids discharged from the nitrator are sent to a back-mix nitrator to complete the nitration.

8. A process as claimed in claim 2 wherein fluids discharged from the nitrator are sent to a gravity settler for separation into an acid layer and a hydrocarbon layer.

9. A process as claimed in claim 2 wherein the heat of nitration and the heat of mixing are removed from the nitrator by external cooling.

10. A process as claimed in claim 2 in which part of the sulfuric acid is recycled sulfuric acid.

11. A process as claimed in claim 2 in which the spent sulfuric acid from the process is reconcentrated by flashing in a vacuum and is recycled to the nitration process.

12. A process as claimed in claim 2 in which the nitratable compound is fed into the process in molar excess of between 0.5% and 25% relative to the nitric acid.

13. A process as claimed in claim 2 in which the nitratable aromatic compound is selected from the group consisting of benzene, toluene, dimethylbenzene, and halogen derivatives, and mononitro derivatives.

14. A process as claimed in claim 2 in which the nitratable compound and feed nitric acid are preheated prior to feeding to the nitrator.

15. A process as claimed in claim 12 in which the nitratable compound is partially vaporized prior to feeding to the nitrator.

* * * * *